(12) United States Patent
Messerschmidt (10) Patent No.: US 8,970,838 B2
(45) Date of Patent: Mar. 3, 2015

(54) METHOD AND APPARATUS FOR EVALUATING A SAMPLE THROUGH VARIABLE ANGLE RAMAN SPECTROSCOPY

(75) Inventor: Robert G. Messerschmidt, Los Altos, CA (US)

(73) Assignee: Avolonte Health LLC, Wilmington, DE (US)

( * ) Notice: Subject to any disclaimer, the term of this patent is extended or adjusted under 35 U.S.C. 154(b) by 759 days.

(21) Appl. No.: 13/098,140

(22) Filed: Apr. 29, 2011

(65) Prior Publication Data

US 2012/0274934 A1 Nov. 1, 2012

(51) Int. Cl.
*G01J 3/44* (2006.01)
*G01N 21/65* (2006.01)
*G01N 21/47* (2006.01)

(52) U.S. Cl.
CPC ........ *G01N 21/65* (2013.01); *G01N 2021/4704* (2013.01)
USPC ............................................ 356/301; 356/73

(58) Field of Classification Search
CPC . G01N 21/658; G01N 21/552; G01N 21/553; G01N 21/554
USPC ...................... 356/445, 72–73, 301
See application file for complete search history.

(56) References Cited

U.S. PATENT DOCUMENTS

| | | |
|---|---|---|
| 3,645,631 A | 2/1972 | Gupta |
| 4,692,024 A | 9/1987 | Bloss |
| 4,730,882 A | 3/1988 | Messerschmidt et al. |
| 5,229,833 A | 7/1993 | Stewart |
| 5,946,083 A | 8/1999 | Melendez et al. |
| 6,141,100 A | 10/2000 | Burka et al. |
| 6,362,144 B1 | 3/2002 | Berman et al. |
| 6,417,924 B1 | 7/2002 | Kimura |
| 6,430,424 B1 | 8/2002 | Berman et al. |
| 6,462,809 B1 | 10/2002 | Ryan et al. |
| 6,493,080 B1 | 12/2002 | Boese |
| 6,493,097 B1 | 12/2002 | Ivarsson |
| 6,690,966 B1 | 2/2004 | Rava et al. |
| 6,748,250 B1 | 6/2004 | Berman et al. |
| 6,841,792 B2 | 1/2005 | Bynum et al. |

(Continued)

FOREIGN PATENT DOCUMENTS

| | | |
|---|---|---|
| CN | 1629618 A | 6/2005 |
| CN | 1749735 A | 3/2006 |

(Continued)

OTHER PUBLICATIONS

"U.S. Appl. No. 12/865,698, Non Final Office Action mailed Mar. 14, 2013", 7 pgs.

(Continued)

*Primary Examiner* — Kara E Geisel
(74) *Attorney, Agent, or Firm* — Schwegman Lundberg & Woessner, P.A.

(57) ABSTRACT

Described are systems and methods for variable angle Raman spectroscopy, in which electromagnetic radiation will be caused to intersect the sample under investigation at a plurality of angles of incidence, so as to provide Raman scattering spectra at each angle. One example use of measuring such spectra at multiple angles of incidence is to enable evaluation at a plurality of depths within the sample. In many implementations, the range of the angles of incidence will include, and extend to either side, of the critical angle.

23 Claims, 5 Drawing Sheets

(56) References Cited

U.S. PATENT DOCUMENTS

| | | | |
|---|---|---|---|
| 6,862,094 | B2 | 3/2005 | Johansen |
| 6,906,327 | B2 | 6/2005 | Shelley et al. |
| 6,908,773 | B2 | 6/2005 | Li et al. |
| 6,992,770 | B2 | 1/2006 | Naya |
| 7,057,731 | B2 | 6/2006 | Naya |
| 7,081,958 | B2 | 7/2006 | Ivarsson |
| 7,154,599 | B2 | 12/2006 | Adams et al. |
| 7,460,236 | B2 | 12/2008 | Ivarsson |
| 7,791,729 | B2 | 9/2010 | Higashi et al. |
| 8,730,468 | B2 | 5/2014 | Messerchmidt |
| 2002/0182743 | A1 | 12/2002 | Perkins et al. |
| 2003/0156278 | A1 | 8/2003 | Yilmaz et al. |
| 2004/0201849 | A1 | 10/2004 | Codner et al. |
| 2005/0214167 | A1 | 9/2005 | Archibald et al. |
| 2005/0229698 | A1 | 10/2005 | Beecroft |
| 2006/0043301 | A1 | 3/2006 | Mantele et al. |
| 2006/0134669 | A1 | 6/2006 | Casasanta, III |
| 2006/0164633 | A1 | 7/2006 | Koshoubu et al. |
| 2006/0187459 | A1 | 8/2006 | Ok et al. |
| 2007/0013912 | A1 | 1/2007 | Ivarsson |
| 2007/0030489 | A1 | 2/2007 | Salamon et al. |
| 2007/0081163 | A1 | 4/2007 | Liang et al. |
| 2010/0153323 | A1 | 6/2010 | Hennessy et al. |
| 2010/0259254 | A1* | 10/2010 | Verschuren et al. .......... 356/445 |
| 2011/0001965 | A1 | 1/2011 | Messerschmidt |
| 2011/0188030 | A1* | 8/2011 | Verschuren et al. .......... 356/128 |
| 2012/0088486 | A1 | 4/2012 | Messerchmidt |

FOREIGN PATENT DOCUMENTS

| | | |
|---|---|---|
| CN | 102460120 B | 7/2014 |
| EP | 1666871 A2 | 6/2006 |
| JP | 04-282435 A | 10/1992 |
| JP | 06505183 A | 6/1994 |
| JP | 06288902 A | 10/1994 |
| JP | 10115573 A | 5/1998 |
| JP | 11-132941 A | 5/1999 |
| JP | 11132941 A | 5/1999 |
| JP | 2000-130353 A | 6/2000 |
| JP | 2001511249 A | 8/2001 |
| JP | 2002-162346 A | 6/2002 |
| JP | 2002174591 A | 6/2002 |
| JP | 3303100 B2 | 7/2002 |
| JP | 2002-530643 A | 9/2002 |
| JP | 2004-500571 A | 1/2004 |
| JP | 2004117298 A | 4/2004 |
| JP | 2004527741 A | 9/2004 |
| JP | 2005502895 A | 1/2005 |
| JP | 2005-241278 A | 9/2005 |
| JP | 2005315680 A | 11/2005 |
| JP | 2006507504 A | 3/2006 |
| JP | 2006189741 A | 7/2006 |
| JP | 2006-201163 A | 8/2006 |
| JP | 2006-317349 A | 11/2006 |
| JP | 2007-127670 A | 5/2007 |
| JP | 2008070391 A | 3/2008 |
| JP | 2008224240 A | 9/2008 |
| JP | 2010520471 A | 6/2010 |
| JP | 2010-156556 A | 7/2010 |
| JP | 2011511292 A | 4/2011 |
| KR | 1020040067322 A | 7/2004 |
| KR | 1020060020036 A | 3/2006 |
| KR | 100628877 B1 | 9/2006 |
| KR | 100668323 B1 | 1/2007 |
| WO | WO-9802730 A1 | 1/1998 |
| WO | WO-9834098 A1 | 8/1998 |
| WO | WO-0029830 A1 | 5/2000 |
| WO | WO-2005088277 A1 | 9/2005 |
| WO | WO-2007/121406 A2 | 10/2007 |
| WO | WO-2009/137122 A2 | 11/2009 |
| WO | WO-2009137122 A1 | 11/2009 |
| WO | WO-2010/118175 A2 | 10/2010 |
| WO | WO-2010/118175 A3 | 10/2010 |
| WO | WO-2012/149343 A1 | 11/2012 |

OTHER PUBLICATIONS

"U.S. Appl. No. 12/865,698, Non Final Office Action mailed Jun. 22, 2012", 7 pgs.

"U.S. Appl. No. 12/865,698, Notice of Allowance mailed Sep. 5, 2013", 8 Pgs.

"U.S. Appl. No. 12/865,698, Notice of Allowance mailed Oct. 16, 2012", 7 pgs.

"U.S. Appl. No. 12/865,698, Notice of Allowance mailed Dec. 26, 2013", 6 pgs.

"U.S. Appl. No. 12/865,698, Preliminary Amendment filed Jul. 30, 2010", 8 pgs.

"U.S. Appl. No. 12/865,698, Response filed Aug. 14, 2013 to Non Final Office Action mailed Mar. 14, 2013", 10 pgs.

"U.S. Appl. No. 12/865,698, Response filed Sep. 24, 2012 to Non Final Office Action mailed Jun. 22, 2012", 10 pgs.

"Australian Application Serial No. 2010234465, First Examination Report mailed Aug. 14, 2012", 2 pgs.

"Australian Application Serial No. 2012249441, Amendment filed Sep. 27, 2013", 9 pgs.

"Canadian Application Serial No. 2,832,045, Voluntary Amendment filed Jan. 7, 2014", 21 pgs.

"Chinese Application Serial No. 200980112418.9, Office Action mailed Nov. 28, 2012", 32 pgs.

"Chinese Application Serial No. 200980112418.9, Response filed Jul. 19, 2012 to Office Action mailed Jan. 5. 2012", (w/ English Translation of Claims), 11 pgs.

"Chinese Application Serial No. 2009801124189, Office Action mailed Jan. 5, 2012", (w/ English Translation), 14 pgs.

"European Application Serial No. 12722961.5, Office Action mailed Jan. 9, 2014", 2 pgs.

"International Application Serial No. PCT/US2009/032706, International Search Report mailed Nov. 27, 2009", 2 pgs.

"International Application Serial No. PCT/US2010/030299, International Preliminary Report on Patentability mailed Oct. 20, 2011", 5 pgs.

"International Application Serial No. PCT/US2010/030299, International Search Report mailed Jan. 31, 2011", 5 pgs.

"International Application Serial No. PCT/US2010/030299, Written Opinion mailed Jan. 31, 2011", 3 pgs.

"International Application Serial No. PCT/US2012/035484, International Preliminary Report on Patentability mailed Nov. 7, 2013", 8 pgs.

"International Application Serial No. PCT/US2012/035484, International Search Report mailed Aug. 23, 2012", 6 pgs.

"International Application Serial No. PCT/US2012/035484, Written Opinion mailed Aug. 23, 2012", 8 pgs.

"Japanese Application Serial No. 2010-545225, Office Action mailed Dec. 20, 2012", (w/ English Translation), 6 pgs.

"Korean Application Serial No. 10-2010-7019454, Office Action mailed May 14, 2012", 10 pgs.

"Korean Application Serial No. 10-2011-7026540, Notice of Preliminary Rejection mailed Nov. 30, 2012", (w/ English Translation), 5 pgs.

"Korean Application Serial No. 2010-7019454, Response filed Sep. 11, 2012 to Office Action mailed May 14, 2012", 21 pgs.

Fontaine, N. H, et al., "Variable-angle internal-reflection Raman spectroscopy for depth-resolvved vibrational characterization of polymer thin films", *Phys. Rev. B*, 57, (1998), 3807-3810.

Greene, P. R, et al., "Total internal reflection Raman spectroscopy of barley leaf epicuticular waxes in vivo", *Colloids and Surfaces B: Biointerfaces*, 45(3-4), (Nov. 10, 2005), 174-180.

Holzer, W., et al., "Raman study on surface layers and thin films by using total reflection experiments", *Journal of Molecular Structure*, 217, (Mar. 1990), 253-264.

Ishizaki, Flimihiko, et al.; "Near-Infrared Attenuated Total Reflection Raman Spectroscopy for Polymer Surface Observation", *Japanese Journal of Applied Physics*, 47, (2008), 1621-1627.

McKee, K., et al., "Development of a scanning angle total internal reflection Raman spectrometer", Review of Scientific Instruments, 81(4), (2010), 043106.

"Chinese Application Serial No. 200980112418.9, Decision mailed Mar. 11, 2014", w/English Translation, 24 pgs.

(56) References Cited

OTHER PUBLICATIONS

"Chinese Application Serial No. 200980112418.9, Office Action mailed Jun. 19, 2013", w/English Translation, 10 pgs.
"Chinese Application Serial No. 201080025328.9, Office Action mailed Aug. 21, 2013", w/English Translation, 21 pgs.
"European Application Serial No. 09743109.2, European Search Report mailed Dec. 19, 2012", 10 pgs.
"European Application Serial No. 10762403.3, Supplementary European Search Report mailed Aug. 7, 2014", 6 pgs.
"International Application Serial No. PCT/US2009/032706, International Preliminary Report on Patentability mailed Aug. 12, 2010", 6 pgs.
"International Application Serial No. PCT/US2009/032706, Written Opinion mailed Nov. 27, 2009", 4 pgs.
"Japanese Application Serial No. 2010-545225, Examiners Decision of Final Refusal mailed Sep. 29, 2014", w/English Translation, 4 pgs.
"Japanese Application Serial No. 2010-545225, Office Action mailed Jan. 29, 2014", w/English Translation, 7 pgs.
"Japanese Application Serial No. 2012-504837, Office Action mailed Aug. 4, 2014", w/English Translation, 4 pgs.
"Japanese Application Serial No. 2012-504837, Office Action mailed Dec. 4, 2013", w/English Translation, 8 pgs.
"Korean Application Serial No. 10-2010-7019454, Notice of Final Rejection mailed Jan. 16, 2013", w/English Translation, 5 pgs.
"Korean Application Serial No. 10-2010-7019454, Office Action mailed Jul. 31, 2013", w/English Translation, 23 pgs.
"Korean Application Serial No. 10-2011-7026540, Notice of Final Rejection mailed May 21, 2014", w/English Translation, 5 pgs.
"Korean Application Serial No. 10-2011-7026540, Notice of Preliminary Rejection mailed Aug. 20, 2013", w/English Translation, 11 pgs.
"Korean Application Serial No. 10-2011-7026540, Notice of Preliminary Rejection mailed Sep. 22, 2014", w/English Translation, 13 pgs.
"Korean Application Serial No. 10-2013-7006842, Notice of Preliminary Rejection mailed Apr. 30, 2014", w/English Claims, 11 pgs.
Rowell, N., et al., "Organic monolayers detected by single reflection attenuated total reflection infrared spectroscopy", Journal of Vacuum Science and Tecnhnology, Part A, 24(3), (2006), 668-672.
Tentori, D., et al., "High-Accuracy Critical Angle Refractometry", Optical Engineering, 32(3), (1993), 593-601.
"Japanese Application Serial No. 2014-508606, Office Action mailed Oct. 20, 2014", (w/ English Translation), 9 pgs.

\* cited by examiner

METHOD AND APPARATUS FOR EVALUATING A SAMPLE THROUGH VARIABLE ANGLE RAMAN SPECTROSCOPY

The present invention relates generally to the evaluation of samples through use of Raman spectroscopy adapted to direct electromagnetic radiation to intersect the sample at a plurality of angles; and more particularly relates to such methods wherein the Raman scattered electromagnetic radiation from a plurality of angles of incidence is used to evaluate one or more properties of the sample under investigation.

BACKGROUND OF THE INVENTION

In conventional Raman spectroscopy, a source of electromagnetic radiation, such as a laser, will be used to excite a sample under investigation with an excitation energy. After contacting the sample, the excitation energy will be scattered. Most of the light scattered by the sample will be scattered elastically; this light is at an unshifted wavelength and may be detected after leaving the specimen. However, a relatively small portion of the laser light is scattered inelastically as a result of coming into contact with the sample. This inelastically scattered light exits the specimen at shifted wavelengths which are at both higher and lower energy states than the original laser wavelength. The light shifted to longer wavelengths is called the Stokes-shifted Raman signal, and the light shifted to shorter wavelengths is called the anti-Stokes Raman signal. The amount of the shift reflects the vibrational spectrum of the sample under examination. This Raman shift spectrum may be detected and analyzed, such as through use of a spectrograph to evaluate one or more properties or characteristics of the sample under examination.

A limitation of current Raman spectroscopy systems is a relatively limited capability to interact with a sample at different depths into the sample. Systems such as confocal Raman probes have been used to provide some variability of depth of investigation. However, these systems are relatively inefficient; and in view of the relatively small amount of Raman scattering signal that is typically available, will not be well-suited to some applications.

SUMMARY OF THE DISCLOSURE

The methods and apparatus described herein provide a novel methodology for variable angle Raman spectroscopy, in which an excitation beam of electromagnetic radiation will be caused to intersect the sample under investigation at a plurality of angles of incidence, so as to provide Raman scattering spectra at each angle. In most examples, the excitation beam will be a single wavelength. In some examples, multiple excitation beams, each at a single wavelength, may be used to excite the sample to induce the Raman scattering. One example use of measuring such spectra at multiple angles of incidence is to enable evaluation at a plurality of depths within the sample. In many examples, the range of the plurality of angles of incidence utilized will be very near the critical angle of incidence; and thus, such methods may be termed "peri-critical Raman spectroscopy." In many examples as described herein, the range of the angles of incidence will include, and extend to either side of, the critical angle.

DETAILED DESCRIPTION

The following detailed description refers to the accompanying drawings that depict various details of examples selected to show how the present invention may be practiced. The discussion addresses various examples of the inventive subject matter at least partially in reference to these drawings, and describes the depicted embodiments in sufficient detail to enable those skilled in the art to practice the invention. Many other embodiments may be utilized for practicing the inventive subject matter than the illustrative examples discussed herein, and many structural and operational changes in addition to the alternatives specifically discussed herein may be made without departing from the scope of the inventive subject matter.

In this description, references to "one embodiment" or "an embodiment," or to "one example" or "an example" mean that the feature being referred to is, or may be, included in at least one embodiment or example of the invention. Separate references to "an embodiment" or "one embodiment" or to "one example" or "an example" in this description are not intended to necessarily refer to the same embodiment or example; however, neither are such embodiments mutually exclusive, unless so stated or as will be readily apparent to those of ordinary skill in the art having the benefit of this disclosure. Thus, the present invention can include a variety of combinations and/or integrations of the embodiments and examples described herein, as well as further embodiments and examples as defined within the scope of all claims based on this disclosure, as well as all legal equivalents of such claims.

For the purposes of this specification, a "processor-based system" or "processing system" as used herein, includes a system using one or more microprocessors, microcontrollers and/or digital signal processors or other devices having the capability of running a "program," (all such devices being referred to herein as a "processor"). A "program" is any set of executable machine code instructions, and as used herein, includes user-level applications as well as system-directed applications or daemons.

Figure 1:
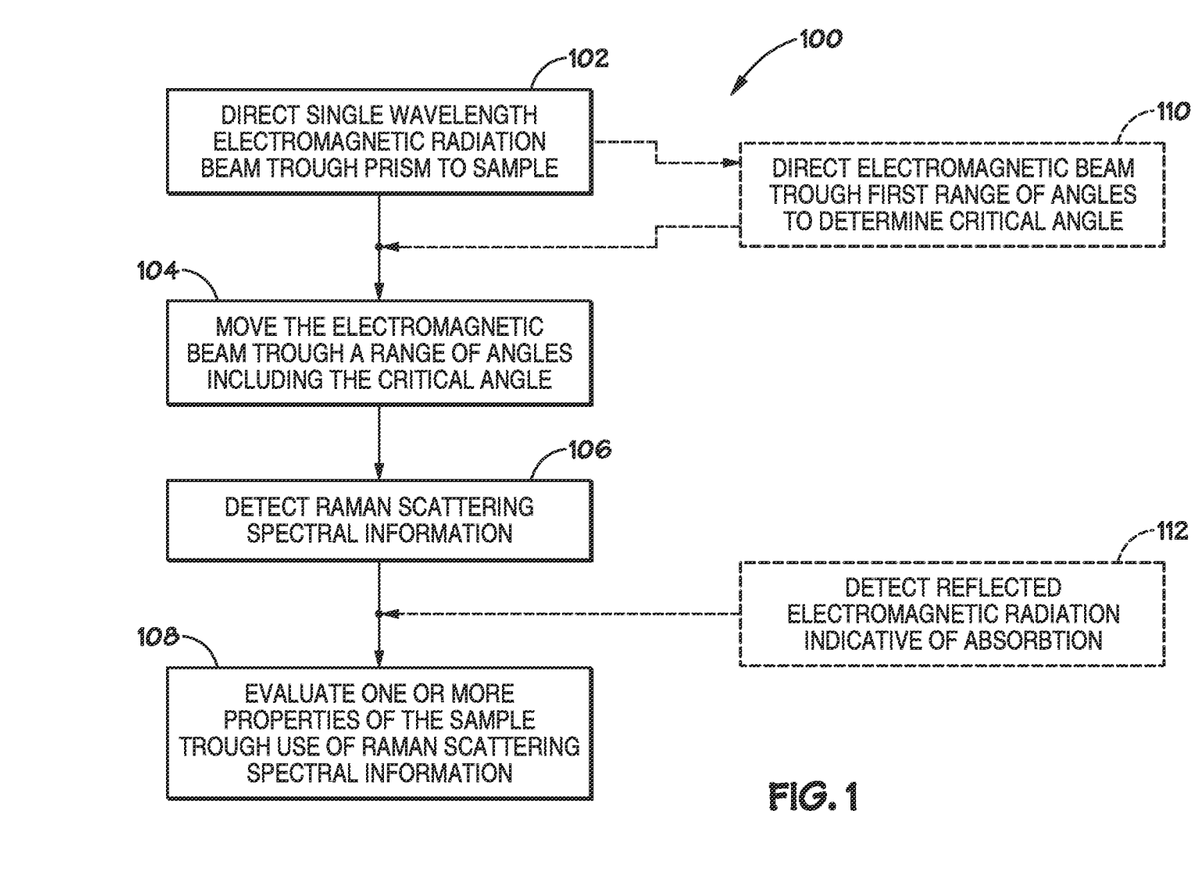
FIG. 1 depicts a flowchart depicting an example method for variable angle Raman spectroscopy as further described herein.

In order to provide an overview of the new methodology, reference is now made to FIG. 1, which depicts a flow chart of an example methodology 100 for peri-critical Raman spectroscopy. In the depicted example method 100, electromagnetic radiation, at a single wavelength, will be directed to transmit through a prism to engage a sample, as indicated at block 102. For purposes this description, the sample will be discussed as a tissue sample, as that is one of many applications in which the described method may advantageously be used.

The path of the electromagnetic beam will be directed, as identified at block 104, such that it intersects the tissue sample at a plurality of angles within a selected range of angles. A primary range of interest will be when the beam is directed at angles of incidence very close to, and including, the critical angle; for example, within a range beginning 0.20 degree above the critical angle or less, such as beginning at 0.10 degree above the critical angle. And in many applications the range will extend through the critical angle of incidence, and for a similar range below the critical angle. The critical angle of incidence for a sample has been discussed in my co-pending, published PCT application No. PCT/US2009/032706, entitled "Methods, Devices and Kits for Peri-Critical Reflectance Spectroscopy." Briefly, when an electromagnetic wave reaches a boundary between two different dielectric constants, part of the wave is reflected and part is transmitted, with the sum of the energies in these two waves equal to that of the original wave. When the light is traversing through a high index medium and approaching an interface with a low index medium, the reflected component can be total, with no light being transmitted. The angle at which this occurs is called the critical angle ($\theta_c$) and is defined by the following equation:

$$\theta_c = \sin-1\left[\frac{n_2}{n_1}\right]$$

Where $n_1$ represents the refractive index of the prism, and $n_2$ represents the refractive index of the sample. In the above range of angles of incidence proximate the critical angle, at the prism/sample interface a strong evanescent wave is formed in the sample, and a traveling wave propagates in a direction parallel to the prism/sample interface plane. Through use of careful constraints on beam divergence, and precise control of increments in the angle of incidence, the evanescent wave can be caused to penetrate to a significant, and variable, distance below the surface of the tissue sample.

As will be apparent from the discussion to follow herein, the manipulation of the beam to cause the described intersection at a plurality of precisely controlled angles can be accomplished through a variety of mechanisms. In some examples, the beam directing mechanism can be relatively direct, such as through use of a precision drive to incrementally rotate (or otherwise change) the position of the source of the electromagnetic beam, which will most commonly be a laser, through a range of positions, such as through a plurality of rotational positions relative to the described prism and tissue sample. Alternatively, however, other beam directing mechanisms may be implemented, such as, for example, directing the electromagnetic beam from the laser (or other source) to the prism through use of one or more mirrors or intermediate deflection prisms, and by moving the mirror(s) (or deflection prisms) through a range of positions relative to the fixed source and fixed prism contacting the sample. In some embodiments, it may also be possible to cause the intersection through a range of angles by changing the position of the prism at the sample; however, in many applications the prism will be in essentially fixed relation to one or more detectors, and the tissue sample may be difficult to move with great precision (such as the body of a patient). Accordingly, in many applications it will be desirable to maintain the prism in a fixed orientation relative to both the tissue sample and at least the detectors in the system. Alternatively, as will be apparent to those skilled in the art, various conventional structures such as mirrors or deflection prisms may be used to direct electromagnetic radiation from the prism to the detector(s) in the system.

At block 106, Raman scattering resulting from intersection of the electromagnetic beam with the sample at each incremental position, and the resulting evanescent wave, will be detected. Ultimately, each detected Raman scattering spectrum will preferably be correlated with the angle of incidence resulting in that spectrum. This detected Raman scattering will typically provide a substantially complete spectrum, at least within a range of interest. As will be understood by those skilled in the art, in many applications it will be desirable to remove detected radiation which is at the frequency of the initial excitation wave, as such does not represent Raman scattered electromagnetic radiation.

The described methods and apparatus for peri-critical Raman spectroscopy described herein are particularly suited to providing vibrational spectroscopy information, thereby reflecting the molecular structure of the sample under consideration. In that context the useful information is obtained in up to 4000 wave numbers of shift. A wavelength of 1μ represents 10,000 wave numbers, and the wavelengths of value are from 1 to 1.6μ, as those light wavelengths will define the 4000 wave number span of useful vibrational spectral information.

At step 108, the detected Raman scattering may be used to evaluate one or more properties or parameters of the sample under investigation. The exact manner by which this evaluation is performed may be at least partially through any of a number of techniques that are known to those skilled in the art. For example, in many applications, the detected scattered electromagnetic spectra may be compared to one or more reference spectra. These reference spectra, depending upon the nature of the reference, may be used to determine the presence or absence of one or more properties, such as variations in the molecular composition of the sample under investigation. In addition to comparing one or more the individual spectra to a reference, all or some portion of the spectrum obtained throughout the range of the angle of excitation may be combined to identify depths within the sample where the data reflects a change in the molecular composition of the sample under investigation. For example, where the described apparatus and techniques are applied to samples of tissue, such as human or other mammalian tissue, a natural example would be examination of the skin One example application would be to examine the skin for spectral patterns which are consistent with spectral patterns observed where a melanoma or similar abnormality is present in the skin.

FIG. 1 also depicts a pair of example additional steps which may optionally be performed in the example method. For example, block 110 describes an operation that may be performed to approximately identify the critical angle, and from that to determine a range of angles to be used in the operation defined at block 104. For example, the electromagnetic beam angle of intersection might be incrementally scanned through a relatively broad range expected to contain the critical angle, for example a range on the order of 4 or 5 degrees; and the incremental positioning might be done at a relatively coarse resolution in order to minimize the time required for scanning across the entire range. For example, a resolution of 0.1 degrees to 0.2 degrees might be used beneficially for some applications. By evaluating the received signal, the critical angle may be determined within a relatively narrow range. Subsequently, the scanning operation of block 104 may be performed over a much more limited range, for example only about 0.10 degrees to either side of the critical angle. However, the resolution of the incremental positioning of each scan across that range may be much smaller. For example, positioning within increments of a fraction of a millidegree is possible with existing hardware. In actual practice, the preferred incremental range may be often within the range of 0.0003 degrees up to 0.01 to 0.02 degrees, for example. In general, deeper depth of sampling is attained by longer wavelength excitation laser light, but with such longer wavelengths, greater angular resolution will be required around the critical angle. Thus the wavelength used and the resolution requirements can be variable in response to the sample being interrogated and/or the needed depth of investigation. In performing the coarse scanning operation of block 110, in some systems which are constructed to include a detector for reflected electromagnetic radiation, it will be possible to use just the reflectance detector to identify the critical angle. Due to the significant difference in the reflected signal at the critical angle, this may allow the coarse scan to be performed, and the data analyzed, relatively efficiently, as compared to collecting all the data of the Raman scattered spectra at each incremental position. In evaluating the light received, the detected radiation, from either Raman scattering or reflection, is processed to correlate the angle of incidence versus the detected intensity of radiation, to determine the inflection point that will identify the critical angle.

To this point, peri-critical spectroscopy has been used in absorption spectroscopy, such as attenuated total reflectance (ATR) spectroscopy. In that usage, peri-critical ATR spectroscopy can provide a specific quantitative measurement, such as the degree of presence of a specific constituent in the sample, where the constituent is one that absorbs light at the excitation wavelength. In contrast, the use of peri-critical Raman spectroscopy as described herein provides an essentially full-spectrum analysis, and thus is better suited to applying a relatively qualitative characterization as to one or more parameters of the sample under investigation.

An advantage of the described methodology is that each obtained spectrum can be representative of a respective depth in the sample, the depth being a function of the angle of incidence and the properties of the resulting evanescent wave. As a result, the Raman-shifted spectral data detected for each incremental angle of incidence can be correlated to provide a three dimensional representation of the sample, wherein a change in the spectral information from one spectrum to another one reflects some change in the molecular composition between the two depths which correlate to the spectra in question. And as noted earlier herein, the spectra of interest may be individually compared with one or more references to identify the sample composition causing the identified change. Additionally, the spectra may be correlated with one another, either in their entirety, or within certain wavelengths of interest to generate a correlated spectrum signal which may be compared to one or more references.

Another advantage of the described methodology is an improvement in the relative volume of Raman scattered light. When a laser beam interacts with tissue, significant scattering can occur. However, internal reflection spectroscopy is relatively immune to the effects of such scattering in tissue; and therefore a greater portion of the returned light is the Raman inelastic scatter. This greater portion of returned Raman scatter allows greater resolution between the Raman scatter and the non-Raman scatter.

Figure 2:
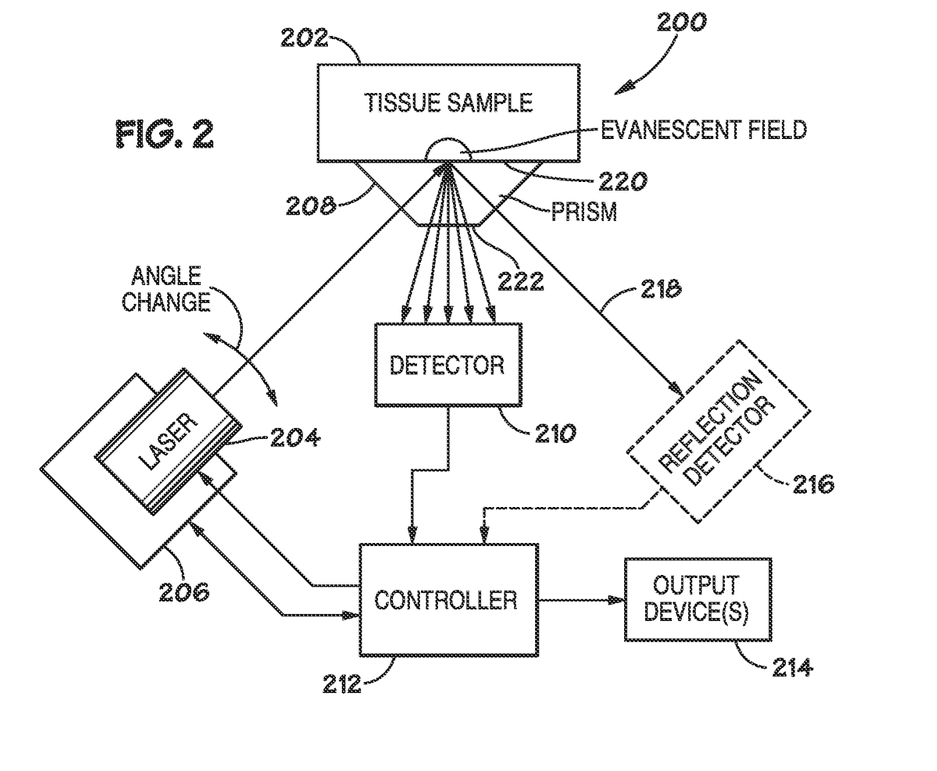
FIG. 2 depicts a block diagram representation of a variable angle Raman spectroscopy system as may be used to perform the method of FIG. 1.

Referring now to FIG. 2, the figure depicts an example peri-critical Raman spectroscopy system 200, depicted in an operative relationship with a sample to be evaluated. In this example, sample 202 will again be described as tissue sample, such as human or other mammal tissue. System 200 includes an illumination source, such as for most applications a laser assembly 204. Laser assembly 204 may optionally include an interferometer or other mechanism to assist in collimating the beam from laser 204. Laser assembly 204 will be mounted on an appropriate mechanism for incrementally moving laser 2042 change the angle of incidence of the laser beam relative to tissue sample 102. An example of one suitable precision drive for incremental control of positioning of laser 204 is the model RGV100 from Newport Corporation of Irvine, Calif. This precision rotational drive is capable of unidirectional repeatability of 0.3 millidegrees.

While many types of lasers may be contemplated for use in spectroscopy system 200, a single diode laser will often be desirable. Such diode lasers can provide a beam of sufficient power for examination of such tissue and can be relatively portable, as may be desired for some applications of the described systems. Where examples of a peri-critical Raman spectroscopy system are intended for use in evaluating human tissue, a significant constraint that will be imposed on the system is the power of the electromagnetic radiation that can be used to excite the sample. These power constraints are subject not only to practical limits, such as levels that would cause pain to a living patient or destruction of the sample; but also often subject to governmental regulations. These constraints will typically limit the power to much lower levels at relatively shorter wavelengths (where the effects of the electromagnetic radiation are relatively more mutagenic or carcinogenic), such that practical or imposed power limits may be fairly low if one is using electromagnetic radiation in the ultraviolet region. However, for wavelengths in the red and infrared spectrum, such power constraints may be on the order of 50 mW. Without excluding the use of electromagnetic radiation at any wavelength, the techniques described herein will commonly be used with radiation within the infrared spectrum, and particularly within the near-infrared and mid-infrared ranges. For purposes of the present description, the mid-infrared range will be considered to refer to wavelengths in the range of 2.5 to 20 microns; and the near-infrared range will be considered to refer to wavelengths in the range of approximately 700 nm to 2.5 microns. When the described techniques and systems are used to evaluate tissue samples as described in the examples herein, it will often be appropriate to use wavelengths within the range of approximately 700 nm to 1 micron.

Referring again to FIG. 2, the electromagnetic beam is directed through a prism 208 that will have a sample-engaging surface be placed in contact with the sample 202. A number of possible configurations for prism 208 may be contemplated. As just one example, a relatively straightforward configuration will be for the prism to have a cross section in the form of a truncated triangle thereby forming a symmetrical trapezoidal cross section. In the depicted example, the sample-engaging surface 220 extends in parallel relation to a spectra-emitting surface 222, through which the Raman scattered radiation will pass. This configuration for prism 208 will allow the Raman scattered radiation to pass from a spectrally emitting sample through the prism 208 to a detector 210 essentially directly opposite the sample. Additionally, reflected light will transmit along axis 218 to reflection detector 216. Reflection detector 216 is an optional component for system 200, which is indicated by the dashed lines identifying the detector and its connections within the system.

The choice of the material for the prism may vary depending upon the nature of the samples to be examined. For many applications, it will be preferable to have a prism with a refractive index that is higher than that of the sample but only by a relatively small amount. In the case of spectroscopy systems intended for evaluating living human tissue, such tissue will typically have a refractive index falling within a range of approximately 1.33 to 1.5. If we were to assume a 1μ wavelength for the excitation wave, then barium fluoride or zinc sulfide would typically be appropriate choices.

The Raman scatter detector 210 is described in more detail in reference to FIG. 3, below. Raman scatter detector to 10 is essentially a spectrograph configured to detect radiation within the frequency range of interest for the sample and excitation frequency utilized. While a single element detector may be used in some applications, the use of a multiple pixel array detector will be desirable for many applications.

Figure 4:
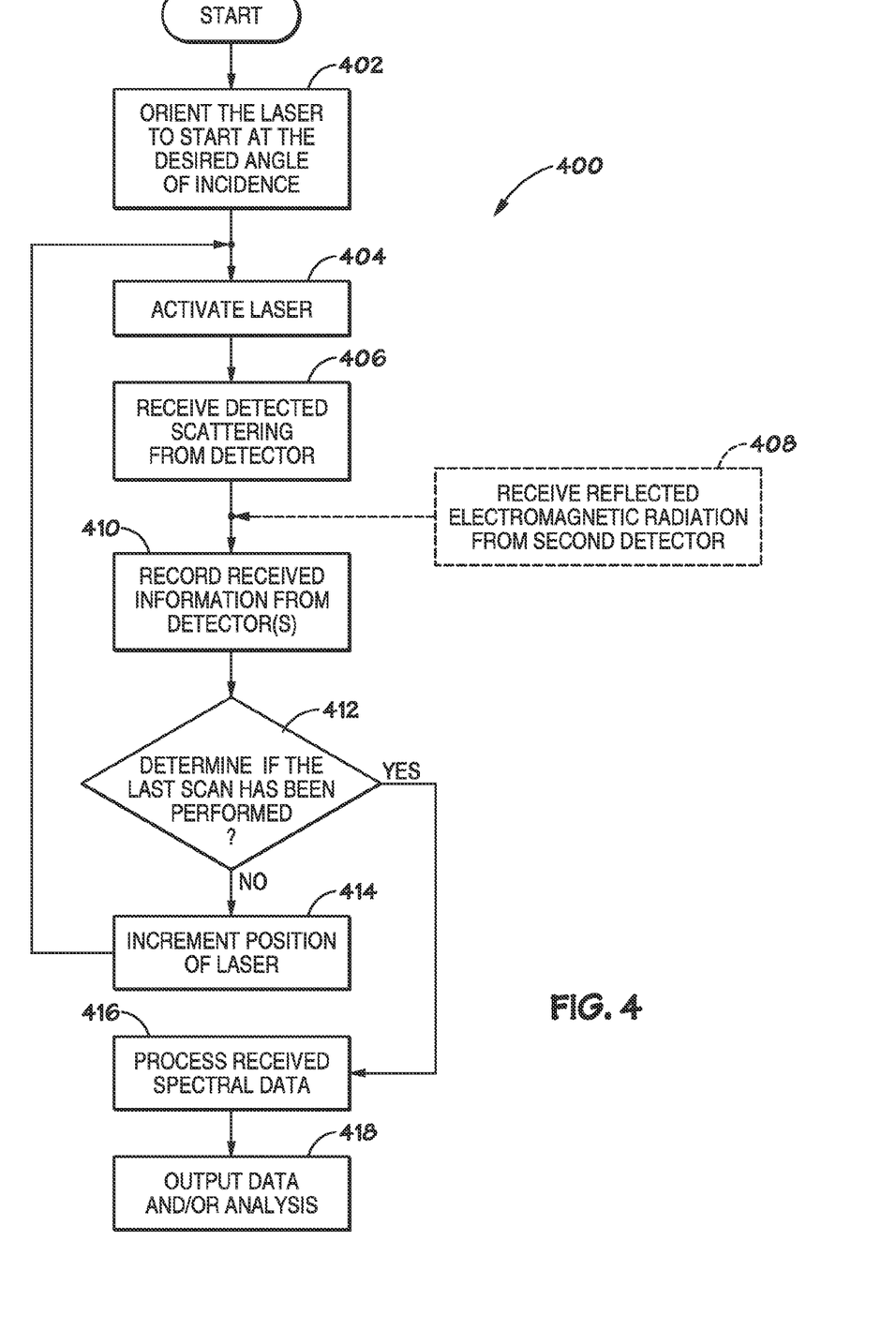
FIG. 4 depicts a flowchart of example functionality of the controller assembly in the system of FIG. 2.

A central controller simply 212 will be used to coordinate the necessary functions for the method as described in reference to FIG. 1. An example flow chart of the basic functionality of controller 212 is depicted in FIG. 4. It should be understood that controller assembly 212 is not necessarily a single device or component, but may be embodied in multiple components that together provide the necessary functionality. In the case where controller assembly is formed a separate components, it should be clearly understood that these components may not be located in one general location, but may be distributed, and connected as needed, for example through one or more networks, including local area networks (LAN), wide area networks (WAN) and/or the Internet. Some or all of the described control functionality may be performed through one or more application programs functioning on a general purpose computer. In other systems, the controller assembly 212 may be a dedicated purpose device, or may include a dedicated purpose device, specifically adapted to provide the necessary functionality. Additionally, the depicted output devices 214 may in fact be a portion of the controller assembly 212, or may be separate components that are not necessarily part of the system at all. For example, the output devices might be remote terminals, printers or databases as may be appropriate to facilitate further analysis, use or maintaining of the acquired data and/or analysis results. Although not absolutely required, it is contemplated that most embodiments of a controller assembly 212 will include one or more processors, with each processor executing a plurality of instructions that are collectively retained in one or more instances of machine-readable storage medium. In most instances these machine-readable storage media will be found within controller assembly 212, however such placement is not mandatory. For example, it is conceivable that the machine-readable instructions might be retained in a machine-readable medium remote from the controller but communicated to the controller assembly 212 across a wired or wireless network.

Figure 3:
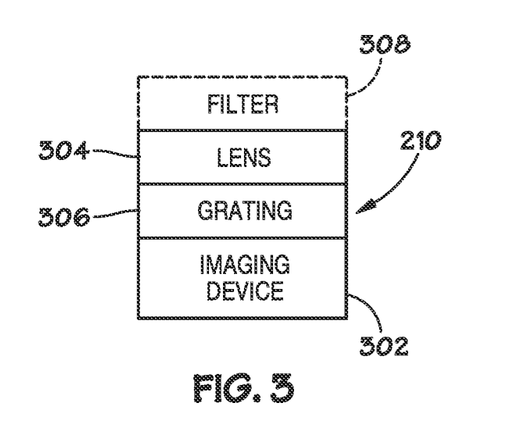
FIG. 3 depicts a block diagram representation of a Raman detector as may be used in the system of FIG. 2.

Referring now to FIG. 3, the figure depicts a block diagram representation of detector 210, which may be a generally conventional spectrograph. Detector 210 will preferably include a relatively high efficiency imaging device 302 so as to capture the relatively small signals typically represented by Raman scattering. For example, a high efficiency CCD or CMOS imager is useful. Additionally, detector 210 will include a lens 304 to capture the elastically scattered light coming from prism 208. As one example of a suitable device, the IXON X3 EMCCD camera, available from Andor Technology of Belfast, Northern Ireland, is suitable for many applications.

Additionally, detector 210 will preferably include a diffraction grating 308. The diffraction grating will split and diffract the impinging light into separate beams. An example of an appropriate grating would be a 1200 line per millimeter grating; which preferably would be a holographic grating. As noted previously, in some applications it will be desirable to filter out incident light at the same wavelength as the original light, as such is not reflective of Raman scattering. In some systems, an appropriate edge filter may be used, wherein the edge filter would either filter the excitation wavelength and all wavelengths below it, or alternatively would filter out the excitation wavelength and all wavelengths about it. As noted previously, in Raman scattering systems you have Stokes scatter to the longer wavelength side, and you have anti-Stokes to the short wavelength sides. In most conventional Raman spectroscopy one does not need to evaluate both the Stokes scatter and the anti-Stokes scatter. However, it is currently contemplated that there may be circumstances in which it would be desirable to look at both the longer and shorter wavelength scatter. In that circumstance a notch filter will be used to filter out just the excitation wavelength, while passing essentially all wavelengths to each side of the excitation wavelength.

Referring now to FIG. 4, the figure depicts a flow chart for basic operations to be performed under control of controller assembly 212. In the example controller functionality 400 of FIG. 4, and initial operation, at block 402, is to orient the laser (or other beam directing mechanism) such that the scan will start at the desired angle of incidence. The start angle of incidence may, in some cases be pre-programmed, or in other cases may be input by a user. Controller assembly 212 will send appropriate signals to orientation device 206 to achieve the desired placement. In addition to controlling the incremental positioning of the beam directing mechanism throughout the range of the scan to be performed, controller assembly 212 track the position of the mechanism and/or monitor the directing mechanism for indication of the position, in order to allow correlation of spectral measurements with the angle of incidence that resulted in each detected spectrum.

Subsequently, at block 404, the laser will be activated for a given time period. In some cases the given time may be a selected interval for discrete measurement. Alternatively, the laser may be left on continually, as it is scanned through the incremental positions of the selected range. Controller assembly 212 will then receive the data representative of detected scattering from detector 210. It will be apparent to those skilled in the art having the benefit of this disclosure that the timing of the receiving of this information by the controller assembly will, at least in most embodiments, not be critical, and the data might be retained in detector 210 for some period of time before being transmitted to controller assembly 212. The data representative of the detected scattering will typically, and often preferably, include the raw detected spectral data. However, it is contemplated that some processing of the data may, in some systems, the performed in the detector; and thus the data representative of the detected scattering may be, or may include, processed spectral data. Additionally, in an optional step, if a reflection detector 216 is included in example system 200 as discussed earlier herein, then reflected light received by detector 216 may also be received, as identified at block 408. Subsequently, the received spectral information from Raman detector 210 and/or from reflection detector 216 will be recorded in some manner. In most embodiments, the recording will include a digital representation of the received information being stored in a machine-readable medium either in or in communication with controller assembly 212.

Subsequently, at block 412, controller assembly 212 will make a determination as to whether the preceding scan position was the end of the range of the scan (ie, whether the last position was the last position within a scan of multiple positions). If the answer is no, controller assembly 212 will increment the position of the laser to the next position within the scan range (at block 414) and the process will return to block 404 to again activate the laser (unless the laser is continuously activated during the scan). Once the system finally determines at block 412 that the preceding scan position was the final position within the scan, then the flow proceeds to block 416 where controller assembly 212 will, in at least some embodiments, perform some degree of processing of the data, as discussed earlier herein. Subsequently, the data and/or the results of the processing will be output to appropriate devices.

It should be understood that although the example flowchart depicts the processing being done at the end of the data collection, there are circumstances where it may be desirable to do some types of processing during the data collection. For example, where the peri-critical Raman spectroscopy system includes a reflection detector, as indicated at 216 in FIG. 2, signals from that detector may be used to monitor the stability of the excitation laser. In some examples, that monitoring would preferably be performed during the scanning of the excitation laser through the selected range. Alternatively, signals from the reflection detector could be used to normalize the intensity of the received Raman scatter spectrum during processing of the scattering data.

Figure 5:
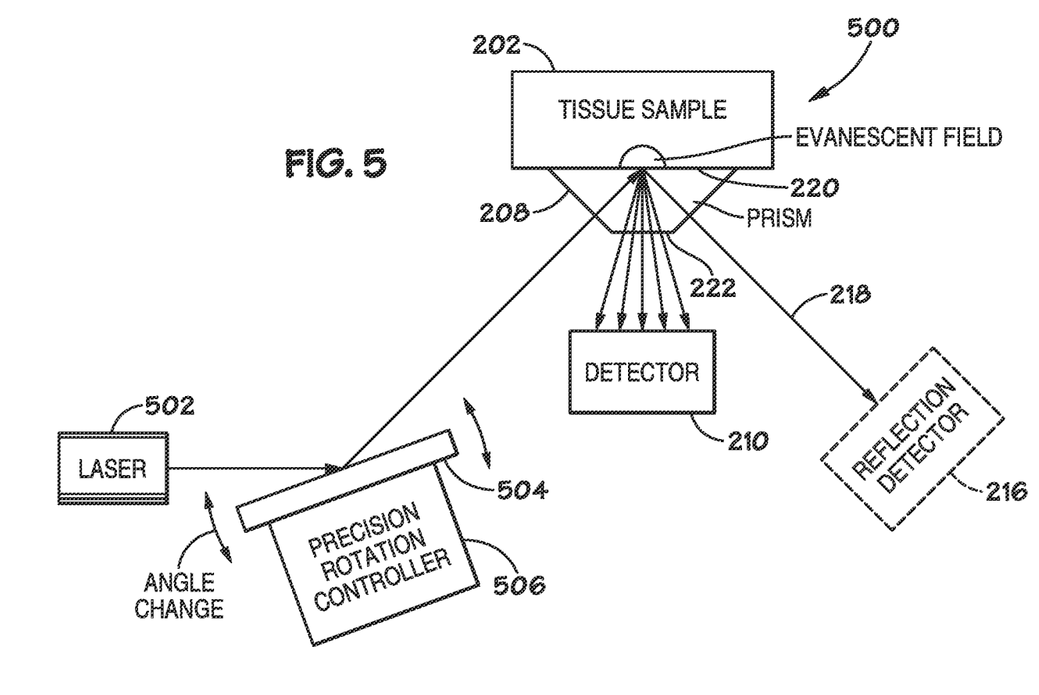
FIG. 5 depicts an alternative configuration for an electromagnetic beam directing assembly.

Referring now to FIG. 5, that figure depicts a block diagram representation of an alternative optical assembly 500 that could be used in a peri-critical Raman spectroscopy system otherwise substantially in the form of that described in reference to FIG. 2. In optical assembly 500, laser 502 is in a fixed position, and is oriented such that the electromagnetic beam may be reflected by a movable mirror (or an intermediate deflection prism) 504 to transmit through prism 208 to tissue sample 202. Movable mirror (or deflection prism) 504 may be mounted on the same form of an precision rotational controller 506 as described in reference to FIG. 2 for use with the laser in that embodiment. Of course, as will be apparent to those skilled in the art, multiple mirrors or deflection prism may be utilized in place of the single assembly depicted in FIG. 5. Additionally, although the deflection assemblies are only depicted relative to the electromagnetic beam input, of course radiation returning from the sample through the prism may also be directed to one or more desired paths toward the one or more detectors through use of similar mirrors or deflection prisms. As will be apparent from the figure, all other basic operation of the optical system remains the same. Some advantages of using this alternative configuration in some applications could include, greater ease of achieving the desired precision of movement, particularly where a given application may dictate the use of a heavier or larger laser or other electromagnetic beam directing assembly.

The illustrative methods and apparatus have been described in the context of using a single wavelength of electromagnetic radiation to excite the tissue sample and cause the Raman scattering. However, it should be clearly understood the same principles can be applied to using multiple discrete wavelengths of electromagnetic radiation to induce Raman scattering and produce respective spectra which may be correlated with those resulting from one or more other wavelengths. In some cases a first wavelength may interact with the sample to provide a first range of penetration into the sample; and a second wavelength may be selected to interact with the sample at either a shallower or deeper depth throughout the contemplated range of angles of incidence. In other cases, the use of multiple wavelengths may be useful in avoiding barriers to effective Raman spectroscopy. For example, with Raman spectroscopy of some types of samples, excitation at certain wavelengths can cause fluorescence, which interferes with effective measurement of Raman scattering. By having multiple wavelengths of excitation, if a first set of scattering data resulting from a first wavelength is less than optimal, such as due to the described fluorescence, the one or more alternative wavelengths may be used to provide satisfactory measurements.

Figure 6:
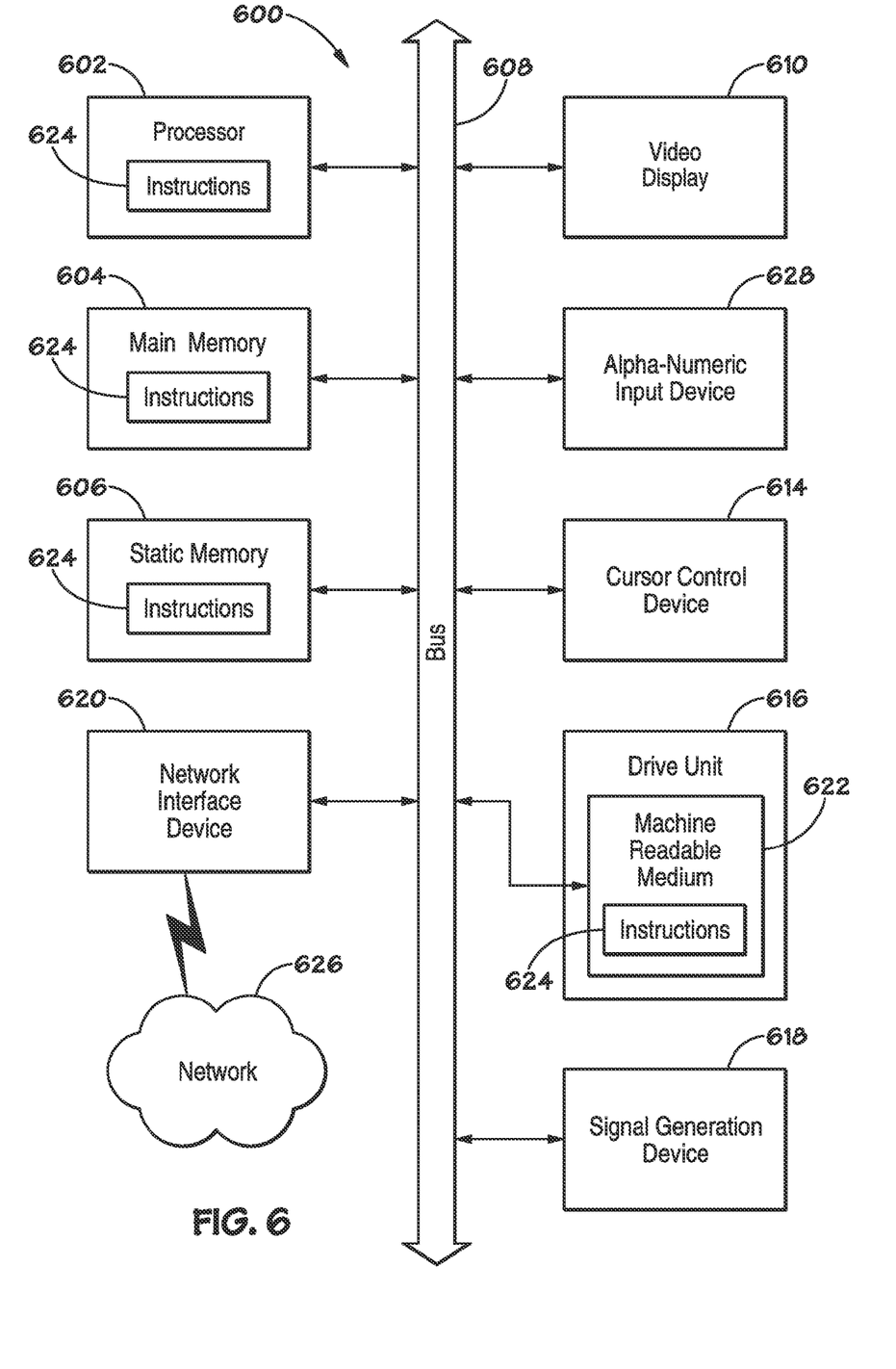
FIG. 6 depicts a block diagram representation of an example of a controller architecture suitable for use in the system of FIG. 2.

Referring now to FIG. 6, that figure depicts block diagram representation of an example architecture for controller 600, such as may be used to provide some or all of the functions of a controller assembly, for which one example was described in reference to FIG. 4. Although not required, in many configurations for the controller assembly 212 would include one or more microprocessors which will operate pursuant to one or more sets of instructions for causing the machine to perform any one or more of the methodologies discussed herein.

The example controller assembly 600 includes a processor 602 (e.g., a central processing unit (CPU) a graphics processing unit (GPU) or both), a main memory 604 and a static memory 606, which communicate with each other via a bus 608. The controller assembly 600 may further include a video display unit 610 (e.g., a liquid crystal display (LCD) or a cathode ray tube (CRT)). The controller assembly 600 also includes an alphanumeric input device 612 (e.g., a keyboard, mechanical or virtual), a cursor control device 614 (e.g., a mouse or track pad), a disk drive unit 616, a signal generation device 618 (e.g., a speaker) and a network interface device 620.

The disk drive unit 616 includes a machine-readable medium 622 on which is stored one or more sets of executable instructions (e.g., software 624) embodying any one or more of the methodologies or functions described herein. In place of the disk drive unit, a solid-state storage device, such as those comprising flash memory may be utilized. The software 624 may also reside, completely or at least partially, within the main memory 604 and/or within the processor 602 during execution thereof by the controller assembly 600, the main memory 604 and the processor 602 also constituting machine-readable media. Alternatively, the instructions may be only temporarily stored on a machine-readable medium within controller 600, and until such time may be received over a network 626 via the network interface device 620.

While the machine-readable medium 622 is shown in an example embodiment to be a single medium, the term "machine-readable medium" as used herein should be taken to include a single medium or multiple media (e.g., a centralized or distributed database, and/or associated caches and servers) that store the one or more sets of instructions. The term "machine-readable medium" or "computer-readable medium" shall be taken to include any tangible non-transitory medium which is capable of storing or encoding a sequence of instructions for execution by the machine and that cause the machine to perform any one of the methodologies.

Many additional modifications and variations may be made in the techniques and structures described and illustrated herein without departing from the spirit and the scope of the present invention. For example, the described methods and systems have been described for measuring properties of tissue, such as skin. However, other types of tissue may also be examined. The described techniques are also contemplated for use such as during surgical procedures, where other tissue may be sufficiently exposed to allow access by an appropriate probe configured to apply an electromagnetic excitation stimulus through a prism, and to detect the resultant Raman scattering, in accordance with the principles discussed herein. Accordingly, the present invention should be clearly understood to be limited only by the scope of the claims and equivalents thereof.

I claim:

1. A method for evaluating a sample, comprising the acts of:

directing an excitation beam of coherent electromagnetic radiation through a prism to intersect a sample at a plurality of angles of incidence, the plurality of angles including a critical angle of incidence;

detecting a Raman scattered spectrum resulting from intersection of the excitation beam with the sample at each of the plurality of angles of incidence; and evaluating at least one property of the sample in reference to at least a portion of the plurality of Raman spectra.

2. The method of claim 1, wherein the act of directing the excitation beam of coherent electromagnetic radiation comprises emitting the beam from a laser.

3. The method of claim 2, wherein the excitation beam of coherent electromagnetic radiation is in the near-infrared range.

4. The method of claim 1, wherein the plurality of angles comprises angles at increments of less than 0.02 degrees proximate the critical angle.

5. The method of claim 1, wherein the prism has a trapezoidal cross-section.

6. The method of claim 1, further comprising the act of recording each Raman scattered spectrum with an imaging device.

7. The method of claim 1, wherein the act of evaluating at least one property of the sample comprises comparing at least one detected Raman spectrum with a reference spectrum associated with the property being evaluated.

8. The method of claim 1, wherein the act of evaluating at least one property of the sample comprises forming a multi-dimensional representation of the sample through use of a plurality of the detected Raman spectra.

9. A method of evaluating a tissue sample, comprising the acts of:

directing a beam of a single wavelength of near-infrared electromagnetic radiation through a prism to intersect the tissue sample, wherein the beam is directed to the sample at a plurality of incremental angles of incidence within a first range, the plurality of incremental angles of incidence including a critical angle of incidence, and wherein the prism is configured to communicate Raman scattered electromagnetic spectra to a detector;

detecting the Raman scattered electromagnetic spectra through use of the detector;

processing the detected electromagnetic spectra to provide a multi-dimensional indication of the molecular composition of the tissue sample at a plurality of depths of investigation.

10. The method of claim 9, wherein the act of directing a beam of near-infrared electromagnetic radiation at a plurality of incremental angles of incidence comprises directing a beam of near-infrared electromagnetic radiation at a first angle of incidence through use of a beam directing mechanism, the first angle of incidence being proximate the critical angle of incidence and to a first side of the critical angle of incidence.

11. The method of claim 10, wherein the beam directing mechanism comprises a movably mounted source electromagnetic radiation.

12. The method of claim 10, wherein the beam directing mechanism comprises a source of electromagnetic radiation and a reflective member between the source of electromagnetic radiation and the prism.

13. A system for evaluating a sample through use of Raman spectroscopy, comprising:

a source of electromagnetic radiation configured to emit a coherent beam of electromagnetic radiation having essentially a single wavelength;

a prism having a sample-engaging surface and a spectra emitting surface;

an electromagnetic beam positioning assembly configured to direct the coherent beam of electromagnetic radiation into the prism at a plurality of angles of incidence relative to the sample engaging surface of the prism, the plurality of angles of incidence including a critical angle of incidence;

a scattering detector arranged to receive scattered electromagnetic radiation from the spectra emitting surface, and configured to record the received scattered electromagnetic radiation; and a controller assembly configured to control the electromagnetic beam positioning assembly to direct the coherent beam electromagnetic radiation at a plurality of controlled angles of incidence at selected angular increments.

14. The system of claim 13, wherein the electromagnetic beam positioning assembly comprises a drive mechanism supporting the source of electromagnetic radiation.

15. The system of claim 13, wherein the electromagnetic beam positioning assembly comprises:

a movable mirror positioned to receive the electromagnetic beam and to reflect the beam in the direction of the prism; and a positioning mechanism supporting the movable mirror, and configured to move the mirror through a range of motion to direct the electromagnetic beam.

16. The system of claim 13, further comprising a reflection detector arranged to receive radiation reflected from the sample through the prism.

17. The system of claim 16, wherein the controller assembly is further configured to receive data representative of Raman scattering spectra received from the scattering detector and to correlate the data representative of each Raman scattering spectrum with the incremental position that resulted in the spectrum.

18. The system of claim 17, wherein the controller assembly is further configured to receive data representative of reflected electromagnetic radiation from the reflection detector.

19. The system of claim 13, wherein the controller assembly comprises:

one or more processors; and a machine-readable medium storing instructions, which when executed by the one or more processors, results in the following operations, orienting the electromagnetic beam positioning assembly to direct the electromagnetic beam at a first angle of incidence relative to the prism sample-engaging surface, activating the laser;

receiving data associated with a plurality of spectra of detected electromagnetic scattering from the scattering detector;

recording the received data from the scattering detector;

orienting the electromagnetic beam positioning assembly to direct the electromagnetic beam at a second angle of incidence, the second angle of incidence being at a determined increment from the first angle of incidence.

20. The system of claim 19, wherein the operations further comprise processing the received data associated with a plurality of spectra of detected electromagnetic scattering to evaluate at least one property of the sample.

21. A system for evaluating a sample through use of Raman spectroscopy, comprising:

a source of electromagnetic radiation configured to emit a coherent beam of electromagnetic radiation having essentially a single wavelength;

a prism having a sample-engaging surface and a spectra emitting surface;

an electromagnetic beam positioning assembly configured to direct the coherent beam of electromagnetic radiation into the prism at a plurality of angles of incidence relative to the sample engaging surface of the prism;

a scattering detector arranged to receive scattered electromagnetic radiation from the spectra emitting surface, and configured to record the received scattered electromagnetic radiation;

a controller assembly configured to control the electromagnetic beam positioning assembly to direct the coherent beam electromagnetic radiation at a plurality of controlled angles of incidence at selected angular increments; and a reflection detector arranged to receive radiation reflected from the sample through the prism;

wherein the controller assembly is further configured to receive data representative of Raman scattering spectra received from the scattering detector and to correlate the data representative of each Raman scattering spectrum with the incremental position that resulted in the spectrum; and wherein the controller assembly comprises:

one or more processors; and machine-readable storage media storing instructions, which when executed by the one or more processors, results in the following operations, orienting the electromagnetic beam positioning assembly to direct the electromagnetic beam at a first angle of incidence relative to the prism sample-engaging surface, activating the laser;

receiving scattering data associated with one or more spectra of detected electromagnetic radiation from the scattering detector;

recording the received scattering data from the scattering detector;

receiving reflected data associated with electromagnetic radiation from the reflection detector;

recording the received reflection data from the reflection detector; and orienting the electromagnetic beam positioning assembly to direct the electromagnetic beam at a second angle of incidence, the second angle of incidence being at a determined increment from the first angle of incidence.

22. The system of claim 21, wherein the operations further comprise processing the received scattering data associated with a plurality of spectra of detected electromagnetic scattering to evaluate at least one property of the sample.

23. The system of claim 21, wherein the operations further comprise processing the received reflection data to evaluate a parameter of the reflection scattering measurement operations.

* * * * *